United States Patent
Tanaka et al.

(10) Patent No.: US 7,583,376 B2
(45) Date of Patent: Sep. 1, 2009

(54) METHOD AND DEVICE FOR EXAMINATION OF NONUNIFORMITY DEFECTS OF PATTERNS

(75) Inventors: Junichi Tanaka, Tokyo (JP); Noboru Yamaguchi, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 10/575,378

(22) PCT Filed: Nov. 17, 2004

(86) PCT No.: PCT/JP2004/017078

§ 371 (c)(1), (2), (4) Date: Aug. 10, 2006

(87) PCT Pub. No.: WO2005/050132

PCT Pub. Date: Jun. 2, 2005

(65) Prior Publication Data

US 2007/0070338 A1    Mar. 29, 2007

(30) Foreign Application Priority Data

Nov. 20, 2003 (JP) ............................. 2003-390821

(51) Int. Cl.
*G01N 21/00* (2006.01)
(52) U.S. Cl. ............ 356/237.2; 356/237.6; 250/559.42; 250/559.44; 382/141; 382/144; 382/145
(58) Field of Classification Search ... 356/237.2–237.6; 250/559.42, 559.44–559.45; 382/141, 144, 382/145
See application file for complete search history.

(56) References Cited

U.S. PATENT DOCUMENTS

| 5,629,768 A * | 5/1997 | Hagiwara ................ 356/237.5 |
| 6,654,113 B2 * | 11/2003 | Fukazawa et al. ........ 356/237.4 |
| 6,727,512 B2 * | 4/2004 | Stokowski et al. ..... 250/559.45 |

FOREIGN PATENT DOCUMENTS

| JP | A 10-300447 | 11/1998 |
| JP | A 2003-297888 | 10/2003 |

* cited by examiner

Primary Examiner—Gregory J Toatley, Jr.
Assistant Examiner—Iyabo S Alli
(74) Attorney, Agent, or Firm—Oliff & Berridge, PLC

(57) ABSTRACT

It is possible to detect with high precision a plurality of types of nonuniformity defects that occur in patterns formed on the surface of an examination object. A device (10) for examination of nonuniformity defects that has a light source (12) for emitting light to a photomask 50 whose surface is provided with a repeating pattern (51) in which unit patterns (53) are arrayed in a regular fashion, and a photodetector (13) for photodetecting and converting into photodetection data scattered light from the photomask, so that the photodetection data is observed to detect nonuniformity defects that have occurred in the repeating pattern, in the device further having a wavelength filter (14) for selecting and extracting one or a plurality of desired wavelength bands from the light of a plurality of wavelength bands, wherein nonuniformity defects of the repeating pattern are detected using the selected and extracted light of the wavelength band.

3 Claims, 5 Drawing Sheets

METHOD AND DEVICE FOR EXAMINATION OF NONUNIFORMITY DEFECTS OF PATTERNS

CROSS REFERENCE TO RELATED APPLICATIONS

This application claims priority of International Application No. PCT/JP04/17078, filed Nov. 17, 2004. The complete disclosure is hereby incorporated by reference.

TECHNICAL FIELD

The present invention relates to method for examination of nonuniformity defects of patterns and a device for examination of nonuniformity defects of patterns, for detecting nonuniformity defects of patterns in image devices and detecting nonuniformity defects of patterns in photomasks for manufacturing patterns of image devices.

BACKGROUND ART

In an image pickup device, display device, or another image device, or in a photomask for manufacturing such devices, nonuniformity defect examination is conventionally available as an option for examining patterns formed on a surface. Nonuniformity defects are errors with a different regularity that has unintentionally occurred in a pattern with a regular arrangement, and these defects occur due to some cause in the manufacturing step or another process.

When nonuniformity defects are present in image pickup devices and display devices, sensitivity nonuniformities and display nonuniformities occur, and the device performance is liable to decrease. When nonuniformity defects occur in photomask patterns that are used in the manufacture of image pickup devices and display devices, the performance of the image device may decrease because the nonuniformity defects are transferred to the pattern of the image device.

Conventionally, nonuniformity defects in photomask patterns and patterns of image devices as described above often cannot be detected in shape examinations of individual patterns due to the fact that microdefects are ordinarily arranged in a regular fashion, but when the area is viewed overall, the defective portion is different than other areas. For this reason, nonuniformity defect examination is mainly carried out by visual examination in oblique light or other examination of the external appearance.

However, since this visual examination has a drawback in that there is variation in the examination result depending on the worker, a device for examination of nonuniformity defects such as that in JP-A 10-300447, for example, has been proposed. The device for examination of nonuniformity defects of JP-A 10-300447 emits light to a substrate on whose surface a pattern is formed, and detects nonuniformity by sensing scattered light from the edge portion of a pattern by using a CCD line sensor.

However, nonuniformity defects include a variety of nonuniformity defects in which the shape, regularity, and other factors are different depending on the cause of the defect or the like, for example. Nevertheless, there is a danger that each of a plurality of types of nonuniformity defects which require detection cannot be detected with high sensitivity in a conventional device for examination of nonuniformity defects that has the device for examination of nonuniformity defects of JP-A 10-300447.

The present invention was contrived with consideration given to the above-described situation, and an object thereof is to provide a pattern nonuniformity defect examination method and a pattern device for examination of nonuniformity defects that can detect with high precision a plurality of types of nonuniformity defects that occur in a pattern formed on the surface of an examination object.

DISCLOSURE OF THE INVENTION

The method for examination of nonuniformity defects of patterns according to a first aspect of the present invention comprises emitting light to an examination object whose surface is provided with a repeating pattern in which unit patterns are arrayed in a regular fashion, photodetecting transmitted light or reflected light from the examination object, and observing the detected photodetection data to detect nonuniformity defects that have occurred in the repeating pattern, wherein the method for examination of nonuniformity defects of patterns further comprises selecting and extracting light of one or a plurality of desired wavelength bands from light of a plurality of wavelength bands, and detecting nonuniformity defects of the repeating pattern by using the light of the selected and extracted wavelength bands.

The method for examination of nonuniformity defects of patterns according to a second aspect of the present invention is the first aspect of the present invention wherein the light of the desired wavelength band to be selected and extracted is light of a wavelength band in which the type of nonuniformity defects that require examination can be detected with high sensitivity.

The method for examination of nonuniformity defects of patterns according to a third aspect of the present invention is the invention according to claim 1 or 2 wherein the examination object is an image device or a photomask for manufacturing the image device.

The device for examination of nonuniformity defects of patterns according to a fourth aspect of the present invention has a light source for emitting light to an examination object whose surface is provided with a repeating pattern in which unit patterns are arrayed in a regular fashion, and a photodetector for photodetecting transmitted light or reflected light from the examination object and converting the light into photodetection data, so that the photodetection data is observed to detect nonuniformity defects that have occurred in the repeating pattern, wherein the device for examination of nonuniformity defects of patterns further has selection and extraction means for selecting and extracting light of one or a plurality of desired wavelength bands from the light of a plurality of wavelength bands, so that nonuniformity defects of the repeating pattern are detected using the light of the selected and extracted wavelength bands.

The device for examination of nonuniformity defects of patterns according to a fifth aspect of the present invention is the invention wherein the light of the desired wavelength band that the selection and extraction means selects and extracts is light of a wavelength band in which the type of nonuniformity defects that require examination can be detected with high sensitivity.

The device for examination of nonuniformity defects of patterns according to a sixth aspect of the present invention is the invention wherein the selection and extraction means is a wavelength filter for selecting, extracting, and directing to the examination object the light of a desired wavelength band from light emitted from a light source.

The device for examination of nonuniformity defects of patterns according to a seventh aspect of the present invention is the invention wherein the selection and extraction means is a wavelength filter for selecting, extracting, and directing to the photodetector the light of a desired wavelength band from light directed from an examination object.

The device for examination of nonuniformity defects of patterns according to an eighth aspect of the present invention is the invention wherein the selection and extraction means is an analysis device for analyzing photodetection data that has been converted in a photodetector, and selecting and extracting photodetection data related to the light of a desired wavelength band from the photodetection data.

The device for examination of nonuniformity defects of patterns according to a ninth aspect of the present invention is the invention wherein the selection and extraction means is provided with a plurality of monochromatic light sources for individually emitting light of a desired wavelength band selected from the light of a plurality of wavelength bands, and is configured to allow the light emission operation of the monochromatic light sources to be switched.

The device for examination of nonuniformity defects of patterns according to a tenth aspect of the present invention is the invention wherein the examination object is an image device, or a photomask for manufacturing the image device.

In accordance with the method and device for examination of nonuniformity defects of patterns of the present invention, since the light of one or a plurality of desired wavelength bands is selected and extracted from the light of a plurality of wavelength bands, and the light of the selected and extracted wavelength bands is observed to detect nonuniformity defects of a repeating pattern, a plurality of types of nonuniformity defects that occur in a repeating pattern can be detected with high precision because each of the types of nonuniformity defects are made apparent and made to stand out to allow observation by using light of different wavelength bands with respect to each of the plurality of types of nonuniformity defects.

Also, in accordance with the method and device for examination of nonuniformity defects of patterns of the present invention, since the light of the desired wavelength bands that is selected and extracted is light of a wavelength band in which the type of nonuniformity defects that require examination can be detected with high sensitivity, nonuniformity defects can be detected with a higher level of precision because nonuniformity defects can be observed and detected by using light of a wavelength band that is suitable for detecting the nonuniformity defects.

BEST MODE FOR CARRYING OUT THE INVENTION

Preferred embodiments for implementing the present invention are described below with reference to the diagrams.

[A] Embodiment 1 (FIGS. 1 and 2)

FIG. 1 is a perspective view showing the general configuration of the first embodiment of the device for examination of nonuniformity defects of patterns of the present invention. FIG. 2 shows nonuniformity defects that have occurred in a repeating pattern in the photomask of FIG. 1; FIGS. 2(A) and 2(B) are diagrams showing the nonuniformity defects of a system with variable coordinate positions; and FIGS. 2(C) and 2(D) are diagrams showing the nonuniformity defects of a dimension-variable system.

The device 10 for examination of nonuniformity defects that is shown in FIG. 1 detects nonuniformity defects that occur in a repeating pattern 51 formed on the surface of a photomask 50 acting as an examination object, and has a stage 11, a light source 12, a photodetector 13, and a wavelength filter 14 that acts as a selection and extraction means. In the present embodiment, the photomask 50 is an exposure mask for manufacturing the photodetector of CCD, for example, which is one type of image device.

Here, examples of the image device include an image pickup device and a display device. Typical image pickup devices include a CCD, CMOS, VMIS, and other solid-state image pickup devices, and typical display devices include a liquid crystal display device, plasma display device, EL display device, LED display device, DMD display device, and other display devices. The photomask 50 is one that is used to manufacture any of these image devices.

The photomask 50 is provided with a chromium film or another light-blocking film on a glass substrate or another transparent substrate 52, and is a photomask in which the light-blocking film has been partially removed in accordance with a desired repeating pattern 51. The repeating pattern 51 has a configuration in which unit patterns 53 are arrayed in a regular fashion.

The method of manufacturing the photomask 50 entails, first, forming a light-blocking film on the transparent substrate 52 and forming a resist film on the light-blocking film. Next, an electron beam or a laser beam of a drawing machine is directed to the resist film, and drawing is carried out to expose a prescribed pattern. The drawing portion and the non-drawing portion are subsequently selectively removed and a resist pattern is formed. The light-blocking film is thereafter etched with the resist pattern acting as a mask, a repeating pattern 51 is formed on the light-blocking film, and the remaining resist is lastly removed to manufacture a photomask 50.

In the manufacturing step described above, seams are generated in the drawing depending on the scan width of the beam and the beam diameter when drawing is carried out directly on the resist film by electron beam or laser beam scanning, and errors due to drawing defects may be periodically produced in the seams in each drawing unit. These errors become the cause of the nonuniformity defects.

An example of the nonuniformity defects is shown in FIG. 2. In FIG. 2, the nonuniformity defect area is indicated by the reference numeral 54. FIG. 2(A) shows a nonuniformity defect caused by a partial difference in the spacing of the unit patterns 53 in the repeating pattern 51 because of the occurrence of beam-induced positional displacement in the seams of the drawing. FIG. 2(B) similarly shows a nonuniformity defect caused by positional displacement of the unit patterns 53 in the repeating pattern 51 with respect to other unit patterns because of the occurrence of beam-induced positional displacement in the seams of the drawing. The nonuniformity defects shown in FIGS. 2(A) and 2(B) are referred to as nonuniformity defects of a system with variable coordinate positions. FIGS. 2(C) and 2(D) show nonuniformity defects in which the unit patterns 53 of the repeating pattern 51 partially increase and decrease in width due to variability in the beam intensity of the drawing machine, or due to other factors. These nonuniformity defects are referred to as nonuniformity defects of a dimension-variable system.

The stage 11 in the device 10 for examination of nonuniformity defects that is shown in FIG. 1 is a platform on which the photomask 50 is mounted. The light source 12 is disposed to one side above the stage 11, and is a unit for emitting light from diagonally above to the repeating pattern 51 of the surface of the photomask 50. In the present embodiment, the light source 12 emits light that includes a plurality of wavelength bands over a broad range, such as white light, and a halogen lamp is used, for example.

The photodetector 13 is disposed to the other side above the stage 11. The photodetector detects light reflected from the repeating pattern 51 of the photomask 50, more particularly, scattered light that has been scattered at the edges of the repeating pattern 51, and converts the light to photodetection data. The photodetector 13 uses a CCD line sensor, a CCD area sensor, or another image pickup sensor, for example. When nonuniformity defects occur in the repeating pattern 51 of the photomask 50, disarrangements occur in the regularity of the photodetection data converted by the photodetector 13. Nonuniformity defects can therefore be detected by observing the photodetection data.

The wavelength filter 14 selects and extracts from the light of a plurality of wavelength bands the light of one or a plurality of desired wavelength bands. More specifically, the wavelength filter 14 is provided with a single-sheet wavelength filter that can individually extract light of a plurality of wavelength bands, or is provided with a plurality of single-sheet wavelength filters that can extract only light of a specific wavelength band. The wavelength filter 14 selects and extracts from light emitted from a light source 12 the light of one or a plurality of desired wavelength bands, and the light of each of the wavelength bands is individually directed to the repeating pattern 51 of the photomask 50.

The light of each of the plurality of wavelength bands that was selected and extracted by the wavelength filter 14 is reflected (scattered) by the repeating pattern 51 of the photomask 50 and is converted to photodetection data by way of the photodetector 13. Nonuniformity defects of the repeating pattern 51 can be observed in the light of the different wavelength bands by observing the photodetection data.

However, a plurality of types of nonuniformity defects that occur in the repeating pattern 51 of the photomask 50 exist because of factors that arise in the manufacturing step and other processes of the repeating pattern 51 as described above. The appearance of the types of nonuniformity defects is different depending on the wavelength band of the observed light in the device 10 for examination of nonuniformity defects, and the light of wavelength bands that can be observed or detected with high sensitivity exists for each type of nonuniformity defect. The light of the desired wavelength band that is selected and extracted by the wavelength filter 14 is light of a waveband in which the types of nonuniformity defects that require examination can be detected with high sensitivity. The light is blue light (light in the vicinity of 440 to 500 nm), green light (light in the vicinity of 500 to 570 nm), or red light (light in the vicinity of 620 to 700 nm), or may be monochromatic light such as laser light, for example. In other words, blue light is set to allow nonuniformity defects of the system with variable coordinate positions shown in FIGS. 2(A) and 2(B) to be detected with high sensitivity, and green light is set to allow nonuniformity defects of the dimension-variable system shown in FIGS. 2(C) and 2(D) to be detected with high sensitivity. The nonuniformity defects can thereby be detected with high sensitivity by using light of a wavelength band that is suited to the type of nonuniformity defect.

Described next is a method of detecting nonuniformity defects of a repeating pattern 51 in a photomask 50 in which the device 10 for examination of nonuniformity defects is used.

The wavelength filter 14 selects and extracts the light of one or a plurality of desired wavelength bands from the light of a plurality of wavelength bands emitted from the light source 12. The wavelength filter 14 individually selects and extracts blue light and green light from the light emitted from the light source 12, for example.

The light of a plurality of desired wavelength bands that is selected and extracted by the wavelength filter 14 is individually reflected by the repeating pattern 51 in the photomask 50. More particularly, scattered light that has been scattered at the edges of the repeating pattern 51 is detected by the photodetector 13 and converted to photodetection data. The photodetection data is observed and nonuniformity defects present in the repeating pattern 51 are detected.

When the nonuniformity defects of the system with variable coordinate positions shown in FIGS. 2(A) and 2(B) are present in the repeating pattern 51, a case in which the nonuniformity defect is observed using blue light that has been selected and extracted by the wavelength filter 14 is observed with much higher sensitivity than a case in which the nonuniformity defect is observed using green light that has been selected and extracted by the wavelength filter 14. Therefore, nonuniformity defects of the system with variable coordinate positions can be detected with high precision using blue light.

When the nonuniformity defects of the dimension-variable system shown in FIGS. 2(C) and 2(D) are present in the repeating pattern 51, a case in which the nonuniformity defect is observed using green light that has been selected and extracted by the wavelength filter 14 is observed with much higher sensitivity than a case in which the nonuniformity defect is observed using blue light that has been selected and extracted by the wavelength filter 14. Therefore, nonuniformity defects of the dimension-variable system can be detected with high precision using green light.

The following effects (1) and (2) can be obtained in accordance with the above-described embodiment with the configuration described above.

(1) The wavelength filter 14 selects and extracts light of one or a plurality of desired wavelength bands from the light of a plurality of wavelength bands emitted from the light source 12, the photodetector 13 converts the light of the selected and extracted wavelength bands into photodetection data, and the nonuniformity defects of repeating pattern 51 in the photomask 50 are detected by individually observing the photodetection data. Consequently, a plurality of types of nonuniformity defects that occur in the repeating pattern 51 of the photomask 50 can be detected with high precision because each of the types of nonuniformity defects can be made apparent and clearly observed by using light of different wavelength bands for each of the plurality of types of nonuniformity defects.

As described above, different types of nonuniformity defects can each be detected with high precision, such as in a system with variable coordinate positions and a dimension-variable system, by detecting the nonuniformity defects of the repeating pattern 51 in the photomask 50 by using the light of two different wavelength bands, that is, the blue light and green light that were selected and extracted by the wavelength filter 14, for example.

(2) Since the light (blue light for nonuniformity defects of a system with variable coordinate positions, and green light for nonuniformity defects of a dimension-variable system, for example) of the desired wavelength bands that is selected and extracted by the wavelength filter 14 is light of wavelength bands that allows the types of nonuniformity defects that require examination to be detected with high sensitivity, the nonuniformity defects can be detected with a higher level of precision because the nonuniformity defects can be observed and detected by using light of a wavelength band that is suitable for detecting the nonuniformity defects.

[B] Embodiment 2 (FIG. 3)

FIG. 3 is a perspective view showing the general configuration of the second embodiment of the device for examination of nonuniformity defects of patterns of the present invention. In the second embodiment, the portions that are the same as the first embodiment are assigned the same reference numerals and a description thereof is omitted.

In lieu of the wavelength filter 14 that selects and extracts light of a desired wavelength band from light emitted from the light source 12 in the first embodiment, the device 20 for examination of nonuniformity defects of the second embodiment is provided with a wavelength filter 21 that has the same structure as the wavelength filter 14 as a selection and extraction means that selects and extracts the light of one or a plurality of desired wavelength bands from scattered light that has been scattered by the repeating pattern 51 of a photomask 50, and directs the light to thephotodetector 13.

Also, in this device 20 for examination of nonuniformity defects, since the wavelength filter 21 selects and extracts the light of one or a plurality of desired wavebands from a plurality of wavelength bands, and nonuniformity defects of the repeating pattern 51 can thereby be detected by using the light of different wavelength bands, a plurality of types of nonuniformity defects that occur in the repeating pattern 51 of the photomask 50 can be detected with high precision in the same manner as in effect (1) of the first embodiment.

Different types of nonuniformity defects can each be detected with high precision such as in a system with variable coordinate positions and a dimension-variable system by detecting the nonuniformity defects of the repeating pattern 51 in the photomask 50 by using the light of two different wavelength bands, that is, the blue light and green light that were selected and extracted by the wavelength filter 21, for example.

Also, in this device 20 for examination of nonuniformity defects, the light of the desired wavelength bands that is selected and extracted by the wavelength filter 21 is light (blue light for nonuniformity defects of a system with variable coordinate positions, and green light for nonuniformity defects of a dimension-variable system, for example) of wavelength bands that allow the types of nonuniformity defects that require examination to be detected with high sensitivity. Consequently, nonuniformity defects can be detected with higher precision because nonuniformity defects can be observed and detected by using the light of a wavelength band that is suitable for detecting the nonuniformity defects, in the same manner as in effect (2) of the first embodiment.

[C] Embodiment 3 (FIG. 4)

FIG. 4 is a perspective view showing the general configuration of the third embodiment of the device for examination of nonuniformity defects of patterns of the present invention. In the third embodiment, the portions that are the same as the first embodiment are assigned the same reference numerals and a description thereof is omitted.

The device 30 for examination of nonuniformity defects of the third embodiment analyzes photodetection data that has been detected and converted by the photodetector 13 without using a wavelength filter 14 and a wavelength filter 21 as in the first and second embodiments, and is provided with an analysis device as a selection and extraction means that selects and extracts from the analyzed photodetection data one or a plurality of types of photodetection data on the light of the desired wavelength band. This analysis device analyzes the photodetection data of the white light of the light source 12 that has been detected and converted by the photodetector 13, for example, and individually selects and extracts one or a plurality of types of photodetection data on blue light, photodetection data on green light, and photodetection data on red light.

In this device 30 for examination of nonuniformity defects as well, the analysis device 31 selects and extracts one or a plurality of types of photodetection data on the light of the desired wavelength bands from the photodetection data on the light of a plurality of wavelength bands, and the nonuniformity defects of the repeating pattern 51 can thereby be detected by using photodetection data (photodetection data on blue light and photodetection data on green light, for example) on the light of different wavelength bands. Consequently, a plurality of types of nonuniformity defects in repeating pattern 51 of the photomask 50 can be detected with high precision in the same manner as in effect (1) of the first embodiment.

Different types of nonuniformity defects can each be detected with high precision, such as in a system with variable coordinate positions and a dimension-variable system, by detecting the nonuniformity defects of the repeating pattern 51 in the photomask 50 by using the photodetection data on light of two different wavelength bands, that is, the blue light and green light that were selected and extracted by the analysis device 31, for example.

Also, in this device 30 for examination of nonuniformity defects, the photodetection data on the light of the desired wavelength bands that are selected and extracted by the analysis device 31 is photodetection data (photodetection data on blue light for nonuniformity defects of a system with variable coordinate positions, and photodetection data on green light for nonuniformity defects of a dimension-variable system, for example) on light of wavelength bands that allow the types of nonuniformity defects that require examination to be detected with high sensitivity. Consequently, nonuniformity defects can be detected with higher precision because nonuniformity defects can be observed and detected by using the light of a wavelength band that is suitable for detecting the nonuniformity defects, in the same manner as in effect (2) of the first embodiment.

[D] Embodiment 4 (FIG. 5)

FIG. 5 is a perspective view showing the general configuration of the fourth embodiment of the device for examination of nonuniformity defects of patterns of the present invention. In the fourth embodiment, the portions that are the same as the first embodiment are assigned the same reference numerals and a description thereof is omitted.

In lieu of the wavelength filter 14 and wavelength filter 21 of the first and second embodiments, the device 40 for examination of nonuniformity defects of the fourth embodiment has, as a selection and extraction means, a selection and extraction mechanism 43 that is provided with a plurality of monochromatic light sources 41, 42, and so forth that each individually emit the light of desired wavelength bands selected from light of a plurality of wavelength bands, and that is configured so that the light emission operation of the monochromatic light sources 41, 42, and so forth can be switched. The monochromatic light source 41 emits blue light, and the monochromatic light source 42 emits green light, for example. The monochromatic light sources 41, 42, and so forth may emit monochromatic light such as laser light.

In this device 40 for examination of nonuniformity defects as well, since the monochromatic light sources 41, 42, and so forth in the selection and extraction mechanism 43 individually emit light of desired wavelength bands selected from the light of a plurality of wavebands, and the light emission operation of the light sources can be switched, a plurality of types of nonuniformity defects that occur in the repeating pattern 51 of the photomask 50 can be detected with high precision in the same manner as in effect (1) of the first embodiment because the nonuniformity defects of the repeating pattern 51 can be detected by using the light of different wavelength bands emitted from the monochromatic light sources 41, 42, and so forth.

Different types of nonuniformity defects, such as those that occur in a system with variable coordinate positions and a dimension-variable system can each be detected with high precision by detecting the nonuniformity defects of the repeating pattern 51 in the photomask 50 by using the light of two different wavelength bands, that is, the blue light and green light that were selected and extracted by the selection and extraction mechanism 43, for example.

Also, in this device 40 for examination of nonuniformity defects, the light of the desired wavelength bands that is individually emitted by the monochromatic light sources 41, 42, and so forth in the selection and extraction mechanism 43 is light (blue light for nonuniformity defects of a system with variable coordinate positions, and green light for nonuniformity defects of a dimension-variable system, for example) of wavelength bands that allows the types of nonuniformity defects that require examination to be detected with high sensitivity. Consequently, nonuniformity defects can be detected with higher precision because nonuniformity defects can be observed and detected by using the light of a wavelength band that is suitable for detecting the nonuniformity defects, in the same manner as in effect (2) of the first embodiment.

Described next in detail is a working example of the present invention. In the present working example, the examination object is a photomask that is used as an exposure mask when a CCD photodetector is formed, and a repeating pattern composed of a chromium light-blocking film pattern corresponding to the photodetector is formed on the photomask. Nonuniformity defects were detected in the repeating pattern formed on the photomask by using the device 30 for examination of nonuniformity defects (FIG. 4) in the third embodiment.

FIGS. 6 to 8 are graphs that show (for a portion of the area of the photomask) the detection results of nonuniformity defects detected using photodetection data on red light, the photodetection data on green light, and the photodetection data on blue light, respectively, that were analyzed by an analysis device 31 of the device 30 for examination of nonuniformity defects. In the graphs, the horizontal axis shows the distance in a prescribed direction on the photomask, and the vertical axis shows the density of the nonuniformity defects. The values that lie between the −5 and 5 on the vertical axis indicate a prescribed level in which the density of the nonuniformity defects was arbitrarily assigned.

In the examination of the nonuniformity defects in the repeating pattern of the photomask in the present working example, nonuniformity defects were not detected when the photodetection data on red light was used, as shown in FIG. 6. However, the nonuniformity defects could be detected when the photodetection data on green light or the photodetection data on blue light was used, as shown in FIGS. 7 and 8. In the particular case in which the photodetection data on green light was used (FIG. 7), the nonuniformity defects could be detected with high sensitivity. Nonuniformity defects that occurred in the repeating pattern of the photomask were therefore considered to be nonuniformity defects of a dimension-variable system.

In the working example, the device 30 for examination of nonuniformity defects in the third embodiment was used, but no limitation is imposed thereby. More specifically, the same effects as those of the above-described working examples can be obtained when nonuniformity defects are detected in the repeating pattern of a photomask by the individual devices for examination of nonuniformity defects through the use of red light, green light, or blue light that have been individually selected and extracted by the wavelength filter 14 of the device 10 for examination of nonuniformity defects in the first embodiment, by the wavelength filter 21 of the device 20 for examination of nonuniformity defects of the second embodiment, or by the selection and extraction mechanism 43 of the device 40 for examination of nonuniformity defects in the fourth embodiment.

The present invention was described above on the basis of the above-described embodiments and working example, but the present invention is not limited thereby.

The photodetector 13, for example, was described as a unit for detecting light that is scattered at the edges of the repeating pattern 51 in a photomask 50, but the photodetector may also detect light that has been transmitted between the repeating patterns 51 of the photomask 50, and may more particularly detect light that has been diffracted at the edge of the photomask 50 as part of transmitted light.

In the embodiments described above, the examination object is a photomask 50, and the devices 10, 20, 30, and 40 for examination of nonuniformity defects were described as devices for detecting nonuniformity defects that have occurred in a repeating pattern 51 of the photomask 50 for manufacturing an image device, but the examination object may be an image pickup device, a display device, or another image device. In this case, the devices 10, 20, 30, and 40 for examination of nonuniformity defects may also be devices that detect nonuniformity defects that occur in pixel patterns (more specifically, repeating patterns the form a CCD, CMOS, or other photodetectors) that form the image pickup surface in an image pickup device, or nonuniformity defects that occur in pixel patterns (more specifically, thin film transistors of the liquid crystal display panel, facing substrates, color filters, and other repeating patterns) that form the display surface in a display device.

BRIEF DESCRIPTION OF THE DRAWINGS

FIGS. 2(A) and 2(B) are diagrams showing the nonuniformity defects of a system with variable coordinate positions; and FIGS. 2(C) and 2(D) are diagrams showing the nonuniformity defects of a dimension-variable system;

[Explanation of Letters or Numerals]

Figure 1:
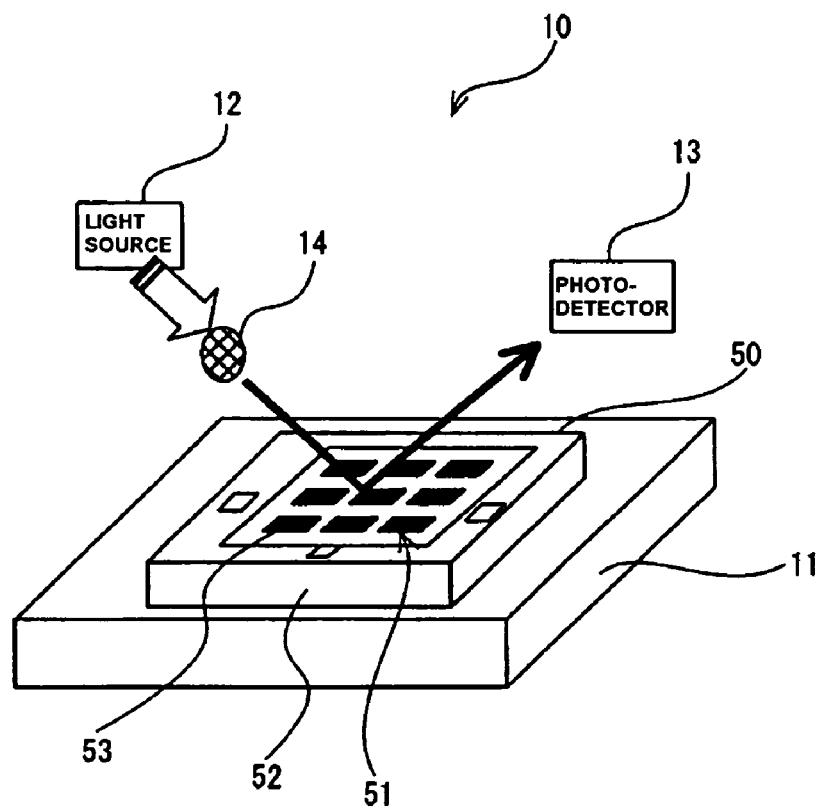
FIG. 1 is a perspective view showing the general configuration of the first embodiment of the device for examination of nonuniformity defects of patterns of the present invention.
Figure 2:
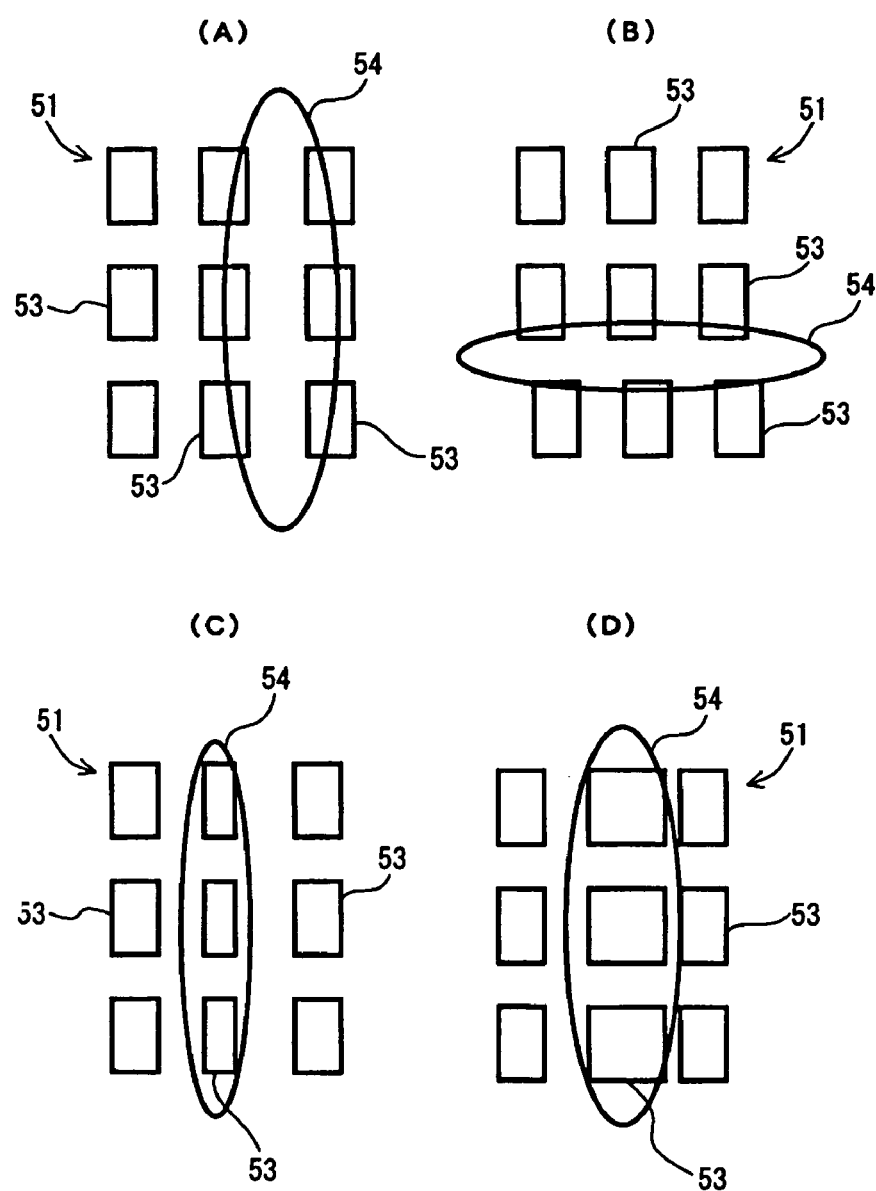
FIG. 2 shows nonuniformity defects that have occurred in a repeating pattern in the photomask of FIG. 1.
Figure 3:
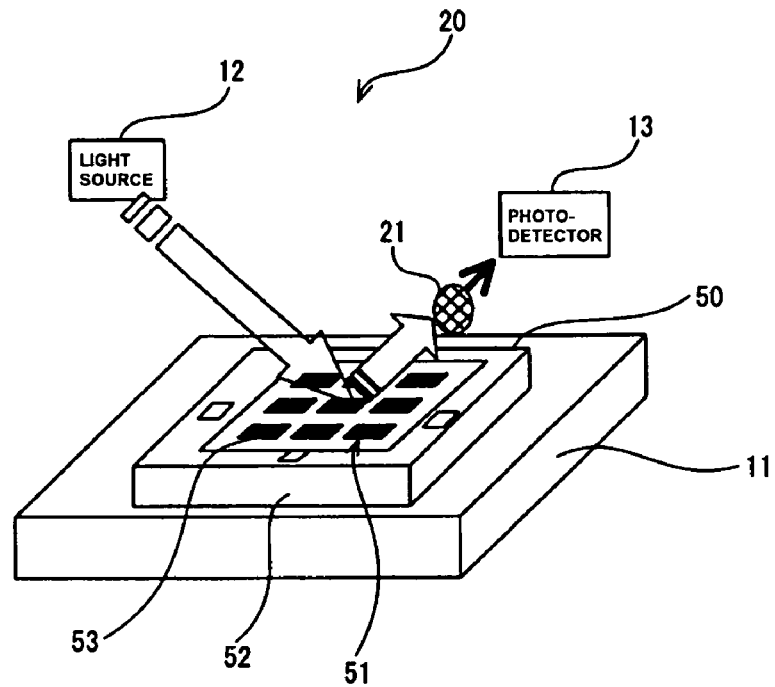
FIG. 3 is a perspective view showing the general configuration of the second embodiment of the device for examination of nonuniformity defects of patterns of the present invention.
Figure 4:
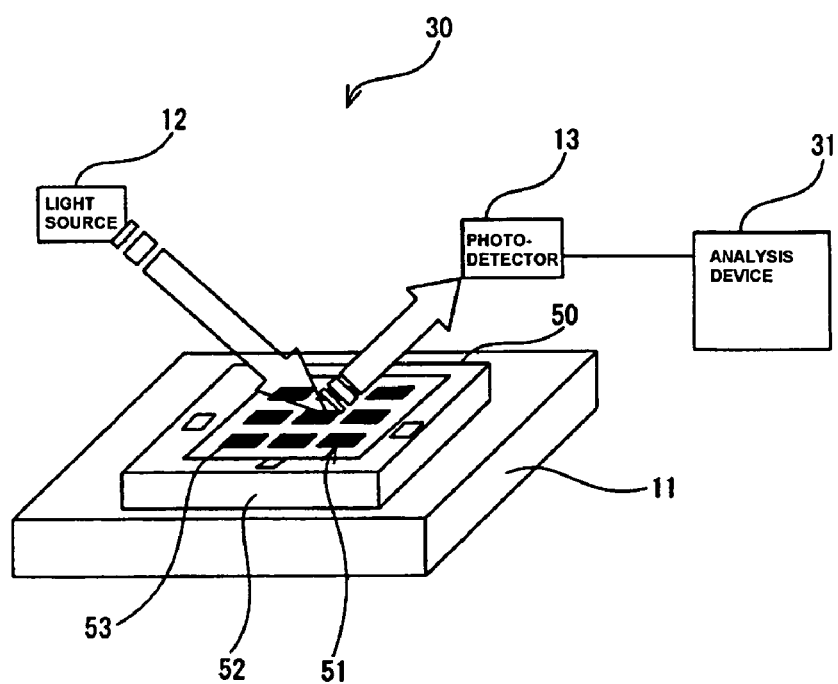
FIG. 4 is a perspective view showing the general configuration of the third embodiment of the device for examination of nonuniformity defects of patterns of the present invention.
Figure 5:
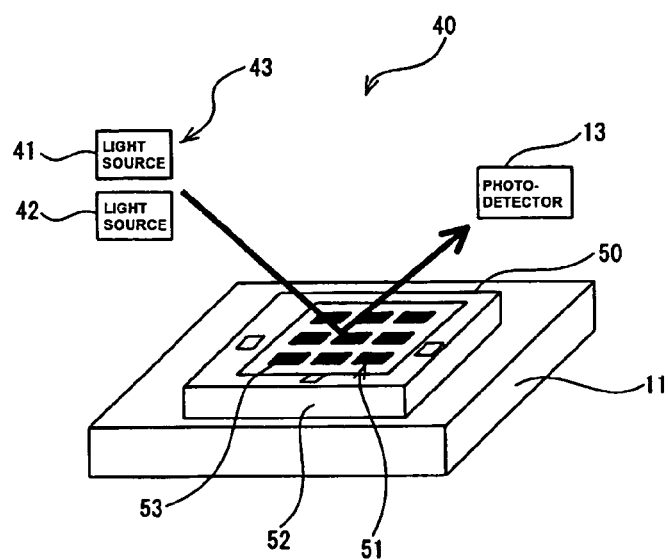
FIG. 5 is a perspective view showing the general configuration of the fourth embodiment of the device for examination of nonuniformity defects of patterns of the present invention.
Figure 6:
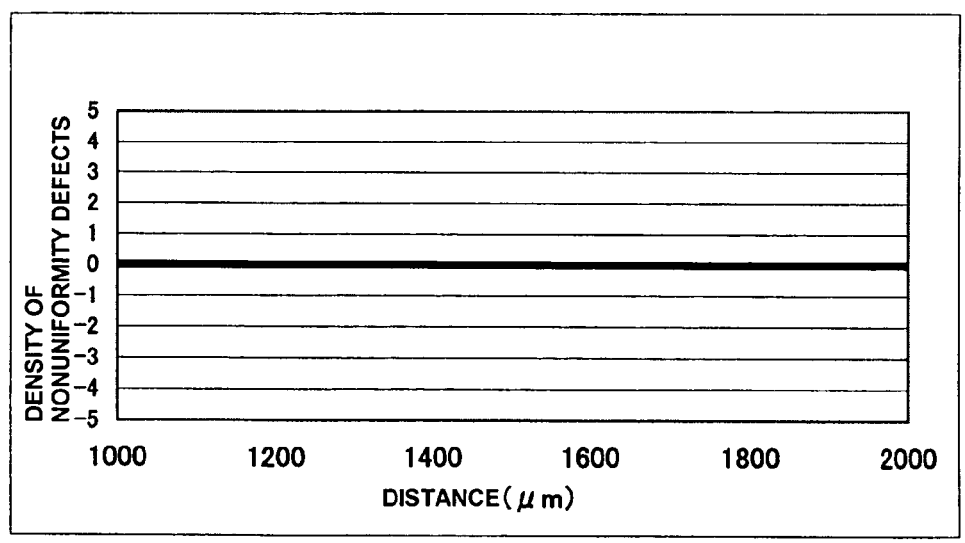
FIG. 6 is a graph showing the detection results of nonuniformity defects detected using red light in the working example.
Figure 7:
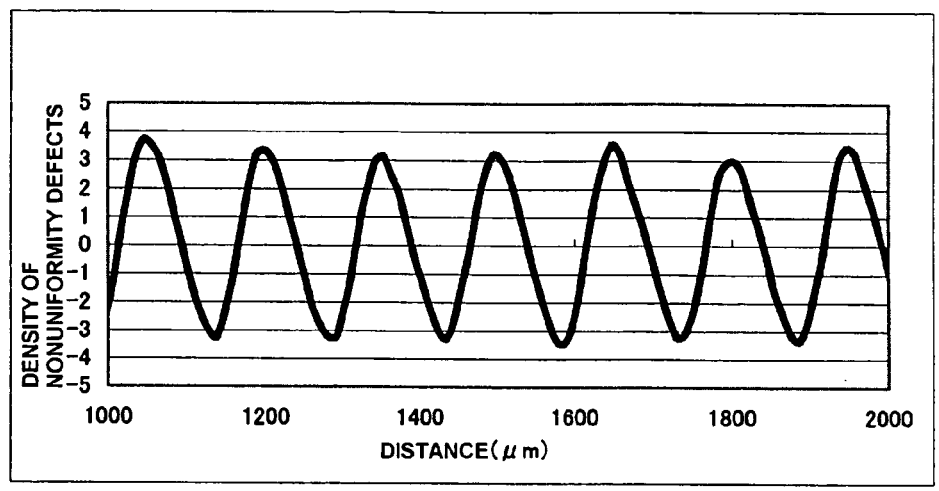
FIG. 7 is a graph showing the detection results of nonuniformity defects detected using green light in the working example.
Figure 8:
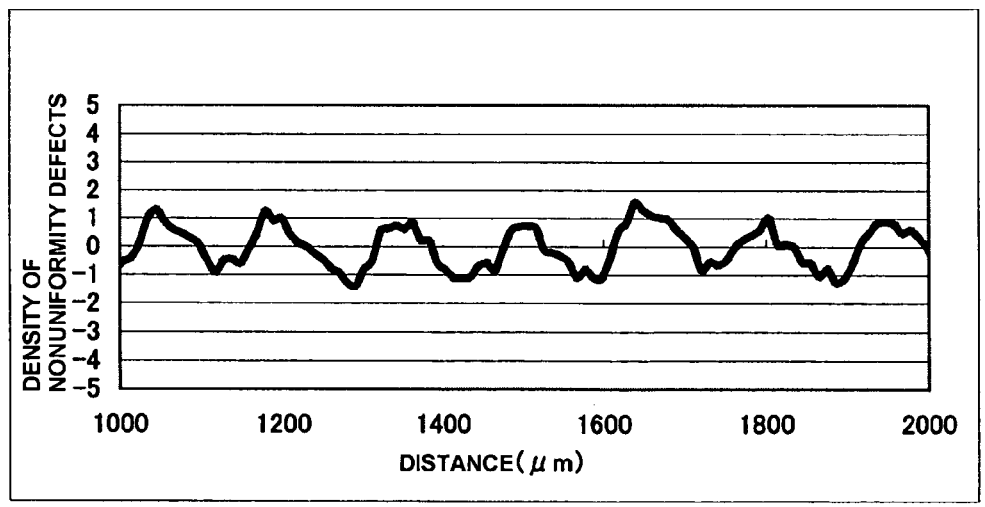
FIG. 8 is a graph showing the detection results of nonuniformity defects detected using blue light in the working example.

10 device for examination of uniformity defects (device for examination of uniformity defects of patterns)
12 light source
13 photodetector
14 wavelength filter (selection and extraction means)
20 device for examination of uniformity defects (device for examination of uniformity defects of patterns)
21 wavelength filter (selection and extraction means)
30 device for examination of uniformity defects (device for examination of uniformity defects of patterns)
31 analysis device (selection and extraction means)
40 device for examination of uniformity defects (device for examination of uniformity defects of patterns)
41, 42 monochromatic light sources
43 selection and extraction mechanism (selection and extraction means)
50 photomask (examination object)
51 repeating pattern
53 unit pattern
54 nonuniformity defect area

The invention claimed is:

1. A method for examination of nonuniformity defects in a photomask pattern for manufacturing an image device, the photomask pattern including a repetitive pattern having a plurality of unit patterns arranged according to a regularity, the method comprising:
   emitting light to the plurality of unit patterns to generate diffraction light at an edge portion of the repetitive pattern;
   photodetecting the diffraction light to produce a photodetection data; and
   observing the photodetection data to determine nonuniformity defects, the nonuniformity defects occurring in the plurality of unit patterns according to another regularity,
   wherein the light comprises a monochromatic laser light having a wavelength of 500 to 570 nm, and
   the nonuniformity defects are determined by identifying a disarrangement in the regularity of the photodetection data.

2. A device for examination of nonuniformity defects in a photomask pattern for manufacturing an image device, the photomask pattern including a repetitive pattern having a plurality of unit patterns arranged according to a regularity, the device comprising:
   a light source for emitting monochromatic laser light having a wavelength of 500 to 570 nm to the plurality of unit patterns to generate diffraction light at an edge portion of the repetitive pattern;
   a photodetector for photodetecting the diffraction light to produce a photodetection data so that the nonuniformity defects, which occur in the plurality of unit patterns according to another regularity, are determined by identifying a disarrangement in the regularity of the photodetection data.

3. The device according to claim 2, wherein said light source comprises a plurality of monochromatic light sources for individually emitting light of a desired wavelength band.

* * * * *